(12) United States Patent
Yeager et al.

(10) Patent No.: US 9,824,797 B2
(45) Date of Patent: Nov. 21, 2017

(54) RESISTIVE GRID ELEMENTS HAVING A THERMOSETTING POLYMER

(71) Applicant: GENERAL ELECTRIC COMPANY, Schenectady, NY (US)

(72) Inventors: Gary William Yeager, Niskayuna, NY (US); Uday Prakash Karmarkar, Lawrence Park, PA (US); John Raymond Krahn, Schenectady, NY (US); Laura Susanne Cooper, Erie, PA (US)

(73) Assignee: General Electric Company, Niskayuna, NY (US)

( * ) Notice: Subject to any disclaimer, the term of this patent is extended or adjusted under 35 U.S.C. 154(b) by 75 days.

(21) Appl. No.: 14/577,688

(22) Filed: Dec. 19, 2014

(65) Prior Publication Data

US 2016/0180990 A1    Jun. 23, 2016

(51) Int. Cl.

| | |
|---|---|
| *B32B 3/24* | (2006.01) |
| *C08L 79/08* | (2006.01) |
| *C08G 73/12* | (2006.01) |
| *H01C 1/01* | (2006.01) |
| *B32B 5/00* | (2006.01) |
| *C07D 207/448* | (2006.01) |
| *H01C 1/012* | (2006.01) |
| *H01C 1/14* | (2006.01) |

(Continued)

(52) U.S. Cl.
CPC ............ *H01C 1/012* (2013.01); *C08L 79/085* (2013.01); *H01C 1/01* (2013.01); *H01C 1/14* (2013.01); *B32B 3/266* (2013.01); *B32B 5/00* (2013.01); *B32B 5/02* (2013.01); *B32B 2307/702* (2013.01); *B32B 2398/00* (2013.01); *B32B 2457/04* (2013.01); *C07D 207/448* (2013.01); *C07D 207/452* (2013.01); *C08G 73/1067* (2013.01); *C08G 73/1071* (2013.01); *C08G 73/12* (2013.01); *C08L 79/08* (2013.01); *C08L 2666/20* (2013.01); *C08L 2666/66* (2013.01); *C08L 2666/72* (2013.01); *H01C 7/00* (2013.01); *Y10T 428/24273* (2015.01)

(58) Field of Classification Search
None
See application file for complete search history.

(56) References Cited

U.S. PATENT DOCUMENTS

| | | | |
|---|---|---|---|
| 3,730,946 A | 5/1973 | Heath et al. | |
| 3,763,210 A | 10/1973 | Heath et al. | |

(Continued)

FOREIGN PATENT DOCUMENTS

| | | |
|---|---|---|
| CN | 202258598 U | 5/2012 |

OTHER PUBLICATIONS

McConnell, Vicky P., Resins for the Hot Zone, Parts I & II, Jun. 8, 2009, CompositesWorld.*

(Continued)

*Primary Examiner* — Jeff Vonch
(74) *Attorney, Agent, or Firm* — Pabitra K. Chakrabarti

(57) ABSTRACT

A resistor grid system includes a resistor strip including multiple pins. The resistor grid system also includes an insulation board coupled to the resistor strip through the multiple pins and configured to provide a structural support. The insulation board is made of a composite material. The composite material includes a nitrogen-containing aromatic thermosetting polymeric resin and a filler.

6 Claims, 2 Drawing Sheets

(51) Int. Cl.

| | |
|---|---|
| C07D 207/452 | (2006.01) |
| H01C 7/00 | (2006.01) |
| B32B 3/26 | (2006.01) |
| C08G 73/10 | (2006.01) |
| B32B 5/02 | (2006.01) |

(56) References Cited

U.S. PATENT DOCUMENTS

| | | | |
|---|---|---|---|
| 3,787,475 A | 1/1974 | Heath et al. | |
| 3,808,576 A | 4/1974 | Castonguay et al. | |
| 3,869,499 A | 3/1975 | Heath et al. | |
| 3,972,902 A | 8/1976 | Heath et al. | |
| 3,985,928 A * | 10/1976 | Watanabe | C08G 59/4042 156/307.4 |
| 4,001,186 A | 1/1977 | Onder | |
| 4,100,140 A | 7/1978 | Zahir et al. | |
| 4,209,458 A | 6/1980 | Keller et al. | |
| 4,223,123 A | 9/1980 | Keller et al. | |
| 4,226,801 A | 10/1980 | Keller et al. | |
| 4,234,712 A | 11/1980 | Keller et al. | |
| 4,238,601 A | 12/1980 | Keller et al. | |
| 4,259,471 A | 3/1981 | Keller et al. | |
| 4,304,896 A | 12/1981 | Keller et al. | |
| 4,307,035 A | 12/1981 | Garvin et al. | |
| 4,315,093 A | 2/1982 | Keller | |
| 4,351,776 A | 9/1982 | Keller et al. | |
| 4,408,035 A | 10/1983 | Keller | |
| 4,409,382 A | 10/1983 | Keller | |
| 4,410,676 A | 10/1983 | Keller | |
| 4,651,125 A * | 3/1987 | Harkness | H01C 3/10 338/295 |
| 4,698,277 A | 10/1987 | Bayer | |
| 5,003,039 A | 3/1991 | Keller | |
| 5,003,078 A | 3/1991 | Keller | |
| 5,004,801 A | 4/1991 | Keller et al. | |
| 5,068,637 A * | 11/1991 | Bayer | B23K 26/24 338/277 |
| 5,120,823 A | 6/1992 | Boyd | |
| 5,132,396 A | 7/1992 | Keller | |
| 5,159,054 A | 10/1992 | Keller | |
| 5,166,290 A * | 11/1992 | Hayashi | C08F 222/40 524/541 |
| 5,202,414 A | 4/1993 | Keller et al. | |
| 5,208,318 A | 5/1993 | Keller | |
| 5,237,045 A | 8/1993 | Burchill | |
| 5,242,755 A | 9/1993 | Keller et al. | |
| 5,247,060 A | 9/1993 | Keller | |
| 5,248,711 A | 9/1993 | Buyny et al. | |
| 5,292,854 A | 3/1994 | Keller | |
| 5,304,625 A | 4/1994 | Keller | |
| 5,350,828 A | 9/1994 | Keller et al. | |
| 5,352,760 A | 10/1994 | Keller | |
| 5,371,236 A * | 12/1994 | Kanayama | C07D 207/452 548/521 |
| 5,389,441 A | 2/1995 | Keller | |
| 5,464,926 A | 11/1995 | Keller | |
| 5,484,880 A * | 1/1996 | Yamashita | C08G 73/1014 528/170 |
| 5,562,971 A | 10/1996 | Yoshiyuki et al. | |
| 5,578,697 A * | 11/1996 | Kawamonzen | C08G 73/1025 257/E23.077 |
| 5,686,880 A * | 11/1997 | Cummins | H01C 3/10 338/280 |
| 5,925,475 A | 7/1999 | Sastri et al. | |
| 5,965,268 A | 10/1999 | Sastri et al. | |
| 6,001,926 A | 12/1999 | Sastri et al. | |
| 6,093,476 A * | 7/2000 | Horiuchi | H01L 21/486 174/255 |
| 6,297,298 B1 | 10/2001 | Keller et al. | |
| 6,756,470 B2 | 6/2004 | Keller et al. | |
| 6,891,014 B2 | 5/2005 | Keller et al. | |
| 7,042,330 B2 | 5/2006 | Nakamura et al. | |
| 7,262,682 B2 | 8/2007 | Ooba et al. | |
| 7,452,959 B2 | 11/2008 | Keller et al. | |
| 7,511,113 B2 | 3/2009 | Keller et al. | |
| 7,592,072 B2 * | 9/2009 | Buyny | B29D 24/005 428/113 |
| 7,937,832 B2 | 5/2011 | Oda et al. | |
| 7,976,956 B2 | 7/2011 | Suzuki et al. | |
| 8,043,697 B2 | 10/2011 | Murakami et al. | |
| 8,202,606 B2 * | 6/2012 | Krahn | H01C 1/08 428/131 |
| 8,409,692 B2 | 4/2013 | Krahn | |
| 8,686,162 B2 * | 4/2014 | Dershem | C08F 2/48 548/520 |
| 8,692,647 B2 * | 4/2014 | Bailey | H01C 3/00 338/279 |
| 2008/0255287 A1 | 10/2008 | Laskoski et al. | |
| 2009/0069484 A1 | 3/2009 | Laskoski et al. | |
| 2010/0156215 A1 * | 6/2010 | Goertzen | H02K 5/132 310/87 |
| 2010/0215973 A1 * | 8/2010 | Fedosya | C07D 207/452 428/457 |
| 2011/0244178 A1 * | 10/2011 | Krahn | H01C 1/08 428/131 |
| 2012/0223806 A1 * | 9/2012 | Krahn | H01C 1/08 338/320 |

OTHER PUBLICATIONS

Ji et al., Novel modification of bismaleimide-triazine resin by reactive hyperbranched polysiloxane, Apr. 2010.*
Kuznetsov et al., Perspective Thermally Stable Thermoset Binders for Polymer Composite Materials, Oct. 2010.*
Fallahi et al., DSC Analysis of Thermosetting Polyimides Based on Three Bismaleimide Resin Eutectic Mixtures, Feb. 2011, Iranian Polymer Journal, vol. 20(2), pp. 161-171.*
Hergenrother, High Temperature Thermosets, 1999 (no month), NASA.*
Scola, Polyimide/Bismaleimide Resins, Jan. 2012, University of Connecticut, pp. 97-119.*
US Dept of Defense, Composite Materials Handbook-MIL 17: Materials Usage, Design, and Analysis, Jun. 1999, vol. 3, pp. 2-28-2-29.*
Karbhari, Durability of Composites for Civil Structural Applications, Jul. 2005, pp. 102-103.*
Mangalgiri, Polymer-matrix Composites for High-temperature Applications, Apr. 2005, pp. 175-193.*
Sugimoto E, "Applications of Polyimide Films to the Electrical and Electronic Industries in Japan", Electrical Insulation Magazine, IEEE, vol. 5, Issue: 1, pp. 15-23, Jan.-Feb. 1989.
Cohen, L.B. "Zircoaluminates Strengthen Premium Ranges of Chemical Coupling Agents," "Plastics Engineering," vol. 39, No. 11, p. 29, Nov. 1983.
Monte, S.J. et al., Coupling Composites with Titanate during Extrusion Processing, Modem Plastics International, pp. 52-54, Jun. 1984.
Monte, S.J. et al., Application of Titanate Coupling Agents in Mineral and Glass Fiber Filled RIM Urethane Systems, Polymer Institute University of Detroit, pp. 187-198.

* cited by examiner

RESISTIVE GRID ELEMENTS HAVING A THERMOSETTING POLYMER

BACKGROUND

Various types of heavy-duty high-current industrial equipment dissipate excess energy through resistor grids in the form of large amounts of heat. For example, resistor grids are used for controlling loads in cranes, for load testing of generators, for harmonic filtering in electric substations, for neutral grounding in industrial AC distribution, for dynamic braking on locomotives and off highway vehicles, and the like.

A resistor grid is an air or oil cooled grid of metal alloy ribbons or plates, formed into a serpentine structure. The ribbons may have engagement pins, along the length of the ribbons or plates, that are inserted into specific pin-holes in an insulation board so as to spatially restrain the ribbons within the grid. The insulation board provides a sturdy frame for the resistor grid and maintains a fixed separation between ribbons, as well as between successive grids when used in a grid stack configuration. The resistor grid provides little electrical resistance and may carry currents ranging from several hundred to thousands of amperes. Neighboring ribbons may have a potential difference of a few volts, but the voltage between parallel runs of the ribbons (or between the ribbons and electrical ground) could be hundreds to thousands of volts. Such operating parameters can cause arcing between neighboring ribbons (or to electrically grounded surfaces such as exhaust louvers) or thermal runaways if the ribbons are too close in proximity or contact one another. Therefore, the structural integrity of the insulation board is an important factor in its construction.

For example, under normal operating conditions, the resistor grids are typically subject to air temperatures between 200 and 400 degrees centigrade. These high temperatures may cause thermal degradation and/or distortion of portions of the insulation board. If portions of the insulation board distorts or degrades, then the pins may be allowed to move from their keyed positions in the insulation board. This may further lead to relative motion of the ribbons, ribbon-to-ribbon contact, electrical arcing, thermal runaway, and subsequent deterioration and ultimate failure of the resistor grid. Accordingly, it is now recognized that materials of construction for the resistor grid insulation boards should exhibit a balance of thermal, mechanical, and abrasion resistance to provide desired reliability.

BRIEF DESCRIPTION

In one embodiment, a resistor grid system is provided. The resistor grid system includes a resistor strip including multiple pins. The resistor grid system also includes an insulation board coupled to the resistor strip through the multiple pins and configured to provide a structural support. The insulation board is made of a composite material. The composite material includes a nitrogen-containing aromatic thermosetting polymeric resin and a filler.

In another embodiment, a method for manufacturing an insulation board of a resistor grid is provided. The method includes adding a filler to a thermosetting polymeric resin to form a molding compound. The method also includes thermosetting the molding compound in a mold to produce a composite. Thermosetting the molding compound includes heating the molding compound above 200° C. The insulation board is made of the composite and does not include a metal supporting structure.

In another embodiment, an insulation board for a resistor grid is provided. The insulation board includes a substantially planar element made of a composite material. The composite material includes a nitrogen-containing aromatic thermosetting polymeric resin and a filler disposed within the nitrogen-containing aromatic thermosetting polymeric resin. The insulation board also includes one or more rows of transverse pin holes disposed along a length of the substantially planar element and configured to engage pins of one or more resistive elements of the resistor grid. The insulation board does not include a metal supporting structure.

BRIEF DESCRIPTION OF THE DRAWINGS

These and other features, aspects, and advantages of the present disclosure will become better understood when the following detailed description is read with reference to the accompanying drawings in which like characters represent like parts throughout the drawings, wherein.

DETAILED DESCRIPTION

Figure 1:
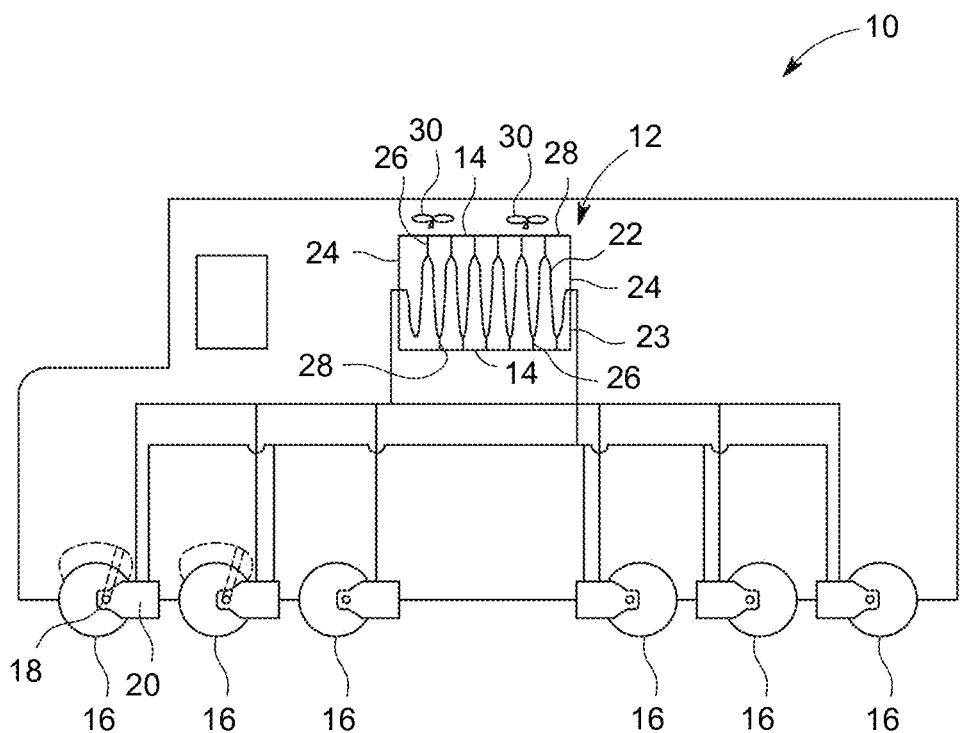
FIG. 1 is an illustration of an embodiment of a locomotive that includes a resistor grid with a pair of insulation boards, in accordance with an aspect of the present disclosure.

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present disclosure, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

As noted above, resistor grids may be subject to air temperatures between 200 and 400 degrees centigrade. These high temperatures may cause thermal degradation and/or distortion of portions of the insulation board. If the insulation board distorts or degrades, then the pins may be allowed to move within their keyed positions in the insulation board. This may further lead to relative motion of the ribbons, ribbon-to-ribbon contact, electrical arcing, thermal runaway, and subsequent deterioration and ultimate failure of the resistor grid. Several techniques have been implemented for the design of resistor grid insulation boards. One such example is a complex board design that includes electrically insulating materials (e.g., resinous materials) with voids where a metal supporting structure is affixed. The metal supporting structure may be inserted into the voids so as to provide additional mechanical stability. The resinous materials provide the thermal, thermal oxidative, and tribological stability of the grid insulation boards. However, it is now recognized that differences in coefficients of thermal expansion between the resinous materials and the metal supporting structure, and potential of interfacial bond failure make manufacture more tedious and the final insulation board less reliable at elevated temperatures.

While certain techniques for the design of resistor grid insulation boards may use a board having a single composite material, materials such as vinyl ester thermosetting resins unexpectedly degrade and exhibit insufficient tribological performance at typical operating temperatures of resistor grids. Moreover, other materials such as phenolic resins exhibit inferior tribological performance and dimensional stability on prolonged exposure to operating temperatures of resistor grids.

On the other hand, present embodiments include single composite materials for construction of resistor grid insulation boards and methods for making resistor grid insulation boards with such materials and without metal supporting structures. In accordance with one aspect of the present disclosure, the composite material may be a curable composition including a thermosetting aromatic polymeric resin and a reinforcement filler for the production of cured composite resistor grid insulation boards. The curable compositions may be further blended with various additives including curing agents, catalysts, inorganic particulate fillers, tougheners, and/or mold release agents. The compound may be molded into a desired shape of the resistor board by, for example, compression molding at elevated temperatures. The materials disclosed herein have a desired balance of properties to provide a resistor grid with adequate mechanical, thermal, and tribological performance.

To help illustrate certain aspects of the present disclosure, present embodiments may be described in the context of certain implementations. However, it should be appreciated that resistor boards produced in accordance with the present disclosure may be used in a number of different contexts, an example of which is provided in FIG. 1. Specifically. FIG. 1 illustrates an embodiment of a locomotive 10 that includes a resistor grid 12 with a pair of insulation boards 14, where the insulation boards 14 are made in accordance with the present disclosure. Although the resistor grid 12 is described in the context of the locomotive 10, it should be noted that the resistor grid 12 may be used in any suitable system, including, but not limited to, cranes, generators, electric stations, power distribution systems, and electrically powered vehicles. As illustrated, the locomotive 10 may include pairs of wheels 16. Each pair of wheels 16 is attached to an axle 18 rotatably coupled to a traction motor 20. The traction motors 20 may connect in parallel with one another.

The illustrated resistor grid 12 includes a resistor strip or bank 22 mounted in a frame 23 including the pair of insulation boards 14 and a pair of side panels 24. The pair of insulation boards 14 may be made of insulating materials, as discussed in greater detail below. The pair of side panels 24 may be made of any suitable insulating materials and/or electrically conducting materials, depending on the configuration of the side panels 24. The resistor strip 22 may include multiple pins or tabs 26, each of which may be received and fixed by a pin hole or cavity 28 disposed in the pair of insulation boards 14.

During operation, the resistor grid 12 may be used during dynamic braking of the locomotive 10. For example, the resistor grid 12 may be electrically connected to the traction motors 20. During operation and particularly during dynamic braking, the traction motors 20 work as generators and provide electrical power to the resistor grid 12. The electrical power is converted to heat by the resistor grid 12 (because of the resistance thereof), and the heat may be dissipated by the resistor grid 12 to an external environment (e.g., using one or more fans 30). The ability of the resistor grid 12 to accept electrical power from the traction motors 20 enables the traction motors 20 to slow the wheels 16.

Figure 2:
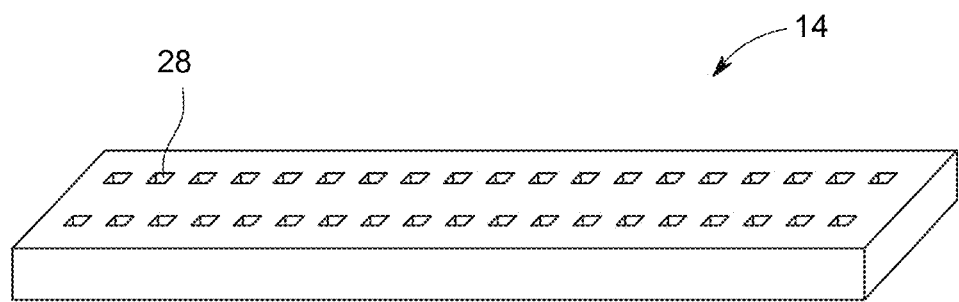
FIG. 2 is a perspective view of an embodiment of the insulation board of FIG. 1, in accordance with an aspect of the present disclosure.

FIG. 2 is a perspective view of an embodiment of the insulation board 14. As will be discussed in greater detail below, the insulation board 14 may be made of an electrical insulation material, in accordance with the present disclosure. The insulation board 14 includes one or more rows of transverse pin holes 28 disposed along a length of the insulation board 14. The pin holes 28 engage the pins 26 of resistive elements of the resistor strip 22 of the resistor grid 12 of FIG. 1. The insulation board 14 provides a substantially rigid support for mounting the resistive elements and maintains a fixed separation between the resistive elements of the resistor grid 12. The durability of the insulation board 14 is one of the most important factors for longevity and proper functioning of the resistor grid 12.

As noted above, the insulation board 14, in accordance with one aspect of the present disclosure, may be made of a single composite including a thermosetting polymer. The insulation board 14 may provide adequate rigidity to the resistor grid 12 without being integrated with any metal supporting structure (e.g., without any voids in the insulation board 14 for receiving any metal supporting structure). As used herein, the metal supporting structure may generally include iron, steel, aluminum, or the like. The metal supporting structures would have comparable dimensions with respect to the insulation board 14 (e.g., between 25% and 100% of a dimension, such as a width, length, or depth of the insulation board 14). In other words, the metal supporting structures are not considered to constitute a filler of a composite.

Figure 3:
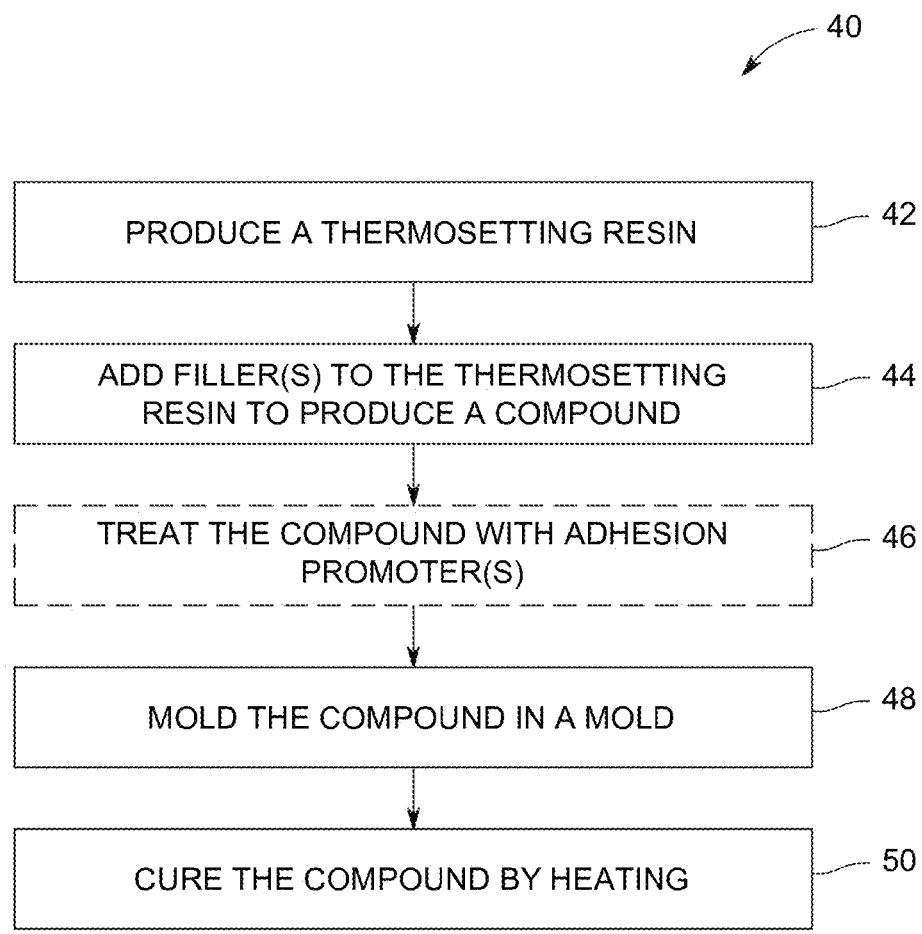
FIG. 3 is a flow diagram of an embodiment of a method of making a composite material for the insulation board of FIG. 1, in accordance with as aspect of the present disclosure.

FIG. 3 is an embodiment of method 40 of making the board using the composite material, in accordance with the present disclosure. Generally, the composite material may be curable and may include a nitrogen-containing aromatic thermosetting resin and a reinforcement filler. The composite material may also include various additives, such as curing agents, catalysts, inorganic particulate fillers, tougheners, and/or mold release agents. The method 40 may start with producing a thermosetting resin (block 42), such as a nitrogen-containing aromatic thermosetting resin. The nitrogen-containing aromatic thermosetting resin may include, by way of non-limiting example, a bismaleimide resin, a polyimide resin, a phthalonitrile resin, or any combination thereof.

Bismaleimide Resin

The thermosetting bismaleimide resins may be formed from bismaleimide monomers. The bismaleimide monomers may be prepared by reacting maleic anhydride or substituted maleic anhydrides with aromatic and/or aliphatic diamines. The bismaleimide monomers as used herein may include any suitable bismaleimide monomers or mixtures thereof. Example bismaleimide monomers may include: N,N'-4,4'-diphenylmethane-bis-maleimide; N,N'-2,4-toluene-bis-maleimide; N,N'-2,6-toluene-bis-maleimide; N,N'-2,2,4-trimethylhexane-bis-maleimide; N,N'-ethylene-bis-maleimide; N,N'-ethylene-bis(2-methyl)maleimide; N,N'-trimethylene-bis-maleimide; N,N'-tetramethylene-bis-maleimide; N,N'-hexamethylene-bis-maleimide; N,N'-1,4-cyclohexylene-bis-maleimide; N,N'-meta-phenylene-bis-maleimide; N,N'-para-phenylene-bis-maleimide; N,N'-4,4'-3,3'-dichloro-diphenylmethane-bis-maleimide; N,N'-4,4'-diphenyl-ether-bis-maleimide; N,N'-4,4'-diphenylsulfone-bis-maleimide; N,N'-4,4'-dicyclohexylmethane-bis-maleimide; N,N'-α,α'-4,4'-dimethylenecyclohexane-bis-maleimide; N,N'-meta-xylene-bis-maleimide; N,N'-para-xylene-bis-maleimide; N,N'-4,4'-diphenyl-cyclohexane-bis-maleimide; N,N'-meta-phenylene-bis-tetrahydrophthalimide; N,N'-4,4'-diphenyl-methane bis-citraconimide; N,N'-4,4'2,2-diphenylpropane-bis-maleimide; N,N'-4,4-1,1-diphenyl-propane-bis-maleimide; N,N'-4,4'-triphenylmethane-bis-maleimide; N,N'-α,α'-1,3-dipropylene-5,5-dimethyl-hydantoin-bis-maleimide; N,N'-4,4'-(1,1,1-triphenyl ethane)-bis-maleimide; N,N'-3,5-triazole-1,2,4-bis-maleimide; N,N'-4,4'-diphenyl-methane-bis-itaconimide; N,N'-para-phenylene-bis-itconimide; N,N'-4,4'-diphenylmethane-bis dimethyl-maleimide; N,N'-4,4'-2,2-diphenylpropane-bis-dimethyl-maleimide; N,N'-hexamethylene-bis-dimethyl-maleimide; N,N'-4,4'-(diphenyl ether)-bis-dimethyl-maleimide; N,N'-4,4'-diphenylsulphone-bis-dimethylmaleimide; N,N'-(oxydi-para-phenylene)-bis-maleimide; N,N'-(oxydi-para-phenylene)-bis-(2-methylmaleimide); N,N'-(methylene di-para-phenylene)-bis-maleimide; N,N'-(methylene di-para-phenylene)-bis-(2-methylmaleimide); N,N'(methylene di-para-phenylene)-bis-(2-phenylmaleimide); N,N'-(sulfonyl di-para-phenylene)-bis-maleimide; N,N'-(thio di-para-phenylene)-bis-maleimide; N,N'-(dithio di-para-phenylene)-bis-maleimide; N,N'-(sulfonyl di-meta-phenylene)-bis-maleimdide; N,N'-(ortho,para-isopropylidene diphenylene)-bis-maleimide; N,N'-(isopropylidene di-para-phenylene)-bis-maleimide; N,N'-(ortho,para-cyclohexylidene diphenylene)-bis-maleimide; N,N'-(cyclohexylidene di-para-phenylene)-bis-maleimide; N,N'-(ethylene di-para-phenylene)-bis-maleimide; N,N'-(4,4"-para-triphenylene)-bis-maleimide; N,N'-(para-phenylenedioxy-di-para-phenylene)-bis-maleimide; N,N'-(methylene di-para-phenylene)-bis-(2,3-dichloromaleimide); and N,N'-(oxy-di-para-phenylene)-bis-(2-chloromaleimide).

The thermosetting bismaleimide resins may include one or more bismaleimide monomers (e.g., as listed above, one or more bismaleimide oligomers, and the like). The one or more bismaleimide monomers may be selected to provide an amorphous resin so as to minimize crystallization of component monomers. "Amorphous," as used herein, refers to a bismaleimide resin that is less than approximately 10% crystalline. In accordance with certain embodiments, the bismaleimide resin may be at least 95% amorphous (e.g., with no more than 5% crystalline), such as at least 96%, 96.5%, 97%, 97.5%, 98%, 98.5%, 99%, or 99.5% amorphous. It may be desired that the bismaleimide resin is at least 99% amorphous (e.g., with no more than 1% crystalline). The degree of crystallization of the bismaleimide resin may be determined by any suitable measurement, such as differential scanning calorimetry.

When the thermosetting bismaleimide resin includes a combination of two or more bismaleimide monomers, the bismaleimide resin combination is desired, but not necessarily, to be a eutectic mixture. A eutectic mixture is one where the melting point of the mixture is at a minimum and less than the melting point of the individual bismaleimide monomers. There may be two or more different bismaleimide monomers in the eutectic mixture.

In some embodiments, the number of bismaleimide monomers in the bismaleimide resin may be less than three. In others embodiments, the number of bismaleimide monomers in the bismaleimide resin may be three or more. The specific combination of three or more bismaleimides that may be used to make the bismaleimide resin may include those that provide an amorphous and eutectic resin when mixed with one another (or additionally in the presence of one or more co-curing agents, thermoplastic toughening agents, and/or resin distribution stabilizers, as discussed in detail below). In embodiments where the bismaleimide resin includes three bismaleimide monomers, a first of the bismaleimide monomers may include: N,N'-4,4'-diphenyl-bis-maleimide; and N,N'-4,4'-diphenyl-ether-bis-maleimide, a second of the bismaleimide monomers may include: N,N'-2,4-toluene-bis-maleimide; N,N'-2,6-toluene-bis-maleimide; and N,N'-meta-phenylene-bis-maleimide, and a third of the bismaleimide monomers may include: N,N'-2,2,4-trimethylhexane-bis-maleimide; and N,N'-4,4'-diphenyl-ether-bis-maleimide. As a specific example of a combination, the bismaleimide resin includes a combination of N,N'-4,4'-diphenyl-bis-maleimide, N,N'-2,4-toluene-bis-maleimide, and N,N'-2,2,4-trimethylhexane-bis-maleimide, or a combination of N,N'-4,4'-diphenyl-bis-maleimide, N,N'-2,6-toluene-bis-maleimide, and N,N'-2,2,4-trimethylhexane-bis-maleimide.

The amounts of each of the bismaleimide monomers included in the bismaleimide resin may vary. Referring to the examples above, it may be desirable that the relative amounts of the bismaleimide monomers in the amorphous mixture are between about 40 to 60 weight percent for the first bismaleimide monomer, between about 20 to 40 weight percent for the second bismaleimide monomer, and about 10 to 20 weight percent for the third bismaleimide monomer. As another example, substantially amorphous eutectic mixtures of three or more bismaleimide monomers may include COMPIMIDE® 353, which is a mixture of N,N'-4,4'-diphenylmethane-bis-maleimide, N,N'-2,4-toluene-bis-maleimide, and N,N'-2,2,4-trimethylhexane-bis-maleimide and commercially available from Degussa/Technochemie (Dossenheim, Germany).

Various other agents, including one or more co-curing agents, toughening agents, diluents, additives, and/or inhibitors may be added to the bismaleimide resin. The co-curing agent may be suitable comonomer able to be combined with bismaleimides. As examples, co-curing agents may include diamines, polyamines, and alkenyl aromatic compounds, such as alkenylphenols and alkenylphenoxyethers. More specific examples include co-curing agents such as alkenylphenols, (e.g., allyl, methallyl and propenyl phenols). Even more specific examples include co-curing agents such as O,O'-diallylbisphenol A and O,O'-dipropenylbisphenol A. As specific examples, the co-curing agent may include o,o'-diallylbisphenol A and TM124. TM124 may be commercially available from Degussa/Technochemie (Dossenheim, Germany) and contains O,O'-diallylbisphenol A. As other specific examples, the co-curing agent may include eugenol, eugenol methylether, and similar compounds, as described in U.S. Pat. No. 4,100,140.

The toughening agent may be any suitable thermoplastic polyimide particles, such as those described in U.S. Pat. Nos. 5,248,711 and 5,120,823. The toughening agent may be formed by the reaction of a dianhydride and a diamine. The polyimide particles may have sizes in the range of approximately 2 micrometers to 100 micrometers, such as between approximately 10 micrometers and 20 micrometers. The polyimide particles may be formed by crushing or grinding of the polyimide material under cryogenic conditions. The polyimide particles may also be formed by suspension precipitation. In some embodiments, all or part of the thermoplastic particles may be pre-dissolved in the bismaleimide resin.

The toughening agent may be added in amounts that provide the desired degree of toughening for the resin consistent with performance requirements for each application. Example toughening agents may include MATRIMID®5218, which may be commercially available from Ciba-Geigy (Hawthorne, N.Y.), and High Performance Powder P84 and P84NT, which may be commercially available from Evonik Industries (Lenzing, Austria). MATRIMID®5218 is a polyimide of benzophenone tetracarboxylic dianhydride (BTDA) and 5(6)-amino-1-(4'-aminophenyl)-1,3,3-trimethylindane polyimide. P84 and P84NT powders are polyimides of BTDA and toluenediamine and 4,4'-diaminodiphenylmethane. Other example toughening agents may include polyetherimides, such as ULTEM 1000 and EXUM 035, both of which may be commercially available from General Electric (Pittsfield, Mass.). In one particular embodiment, P84 powder is used as the thermoplastic toughening agent.

Diluents, additives, and/or inhibitors may also be included in the resin, if desired. The diluents may include triallylisocyanurate, N-vinylpyrrolidone, and diallyether bisphenol A. The additives may include peroxide or azo catalysts, and substituted organophosphine salts. The inhibitors may include hydroquinone and catechol. Hydroquinone may be added to the resin in amount up to about 0.5 weight percent of the total resin. Catechol may be used in place of hydroquinone and may be added to the resin in amount up to about 0.1 weight percent of the total resin.

In addition to or in lieu of the bismaleimide resins discussed above, the thermosetting resin may include a thermosetting polyimide resin. The thermosetting polyimide resin may include a condensation product of aromatic carboxylic acid dianhydride monomers or derivatives therefrom, such as pyromellitic dianhydride, 4,4'-oxydiphthalic anhydride, 2,2-bis-[4-(3,4-dicarboxyphenoxy)phenyl]-propane dianhydride, 3,3',4,4'-benzophenonetetracarboxylic acid dianhydride or 3,3',4,4'-tetracarboxybiphenyl dianhydride, with aromatic diamine monomers, such as 4,4'-oxydianiline, 1,4-diaminobenzene, 1,3-diaminobenzene, 1,3-bis-(4-aminophenoxy)benzene, 1,3-bis-(3-aminophenoxy) benzene, methylenedianiline or 3,4'-oxydianiline, and a reactive chainstopper.

The reactive chainstopper is included with aromatic carboxylic acid dianhydride monomers or derivatives and aromatic diamine monomers to produce reactive polyimide oligomers, which, upon heating, crosslink and convert the oligomeric polyimide to a thermosetting resin. The reactive chainstopper may include compounds containing anhydride, carboxylic acid, carboxylic ester or amine functionality, and a reactive alkene or alkyne group. More specifically, the reactive chainstopper may include norbornene dianhydride, norbornene dicarboxylic acid, norbornene dicarboxylic acid monoalkyl ester, maleic anhydride, maleic acid, maleic acid monoalkyl ester, 3-aminophenylacetylene, and phenylethynyl phthalic anhydride.

Examples of the polyimide resins may include PMR 15, RP 46, MVK-19, AFR 700, PMR11-50 PETI-375, PETI-330 (Ube), and Meldin 7000 Series (e.g., 7001, 7003). More specifically, as an example, oligomerization and imidization of an aromatic diamine, such as methylene dianiline, with an aromatic tetracarboxylic acid derivative or dianhydride, such as benzophenone tetracarboxylic acid dimethyl ester, and the reactive chainstopper, such as norbornene dicarboxylic acid monomethyl ester, may produce the norbornene terminated, thermosetting oligomeric polyimide known in the art as PMR-15. As another example, oligomerization and imidization of an aromatic diamine, such as 1,3-bis(3-aminophenoxybenzene)dianiline, with benzophenone tetracarboxylic acid diethylester or dimethyl ester, and 3-aminophenylacetylene may produce acetylene terminated, thermosetting oligomeric polyimide known to the art as Thermid AL-600.

In addition to or in lieu of the bismaleimide resins and the polyimide resins discussed above, the thermosetting resin may also include a phthalonitrile resin. The phthalonitrile resin may include various types of phthalonitrile polymers, such as those described generally in U.S. Pat. Nos. 3,730,946, 3,763,210, 3,787,475, 3,869,499, 3,972,902, 4,209,458, 4,223,123, 4,226,801, 4,234,712, 4,238,601, 4,259,471, 4,304,896, 4,307,035, 4,315,093, 4,351,776, 4,408,035, 4,409,382, 4,410,676, 5,003,039, 5,003,078, 5,004,801, 5,132,396, 5,159,054, 5,202,414, 5,208,318, 5,237,045, 5,242,755, 5,247,060, 5,292,854, 5,304,625, 5,350,828, 5,352,760, 5,389,441, 5,464,926, 5,925,475, 5,965,268, 6,001,926, 6,297,298, 6,756,470, 6,891,014, 7,452,959, 7,511,113, and U.S. Pat. Appl. Pub. Nos. 2008/0255287 and 2009/0069484.

Once the thermosetting resin is prepared, one or more fillers may be added to the thermosetting resin to form a compound (e.g., a molding compound) (block 44). Examples of the fillers may include those described in "Plastic Additives Handbook, 4th Edition," R. Gachter and H. Muller (eds.), P. P. Klemchuck (assoc. ed.), Hansen Publishers, New York 1993. The one or more fillers may include a granular (e.g., particulate) filler and/or a fibrous filler. A granular filler is herein defined as a filler having an average aspect ratio less than about 5:1. Non-limiting examples of granular fillers may include silica powder, such as fused silica and crystalline silica; boron-nitride powder and boron-silicate powders; alumina; magnesium oxide (or magnesia); wollastonite including surface-treated wollastonite, calcium sulfate (or its anhydride, dihydrate or trihydrate), calcium carbonate including chalk, limestone, marble and synthetic, precipitated calcium carbonates, generally in the form of a ground granular (e.g., including 98+% $CaCO_3$ and the remainder being other inorganics, such as magnesium carbonate, iron oxide, and alumino-silicates); surface-treated calcium carbonates; talc, including fibrous, modular, needle shaped, and lamellar talc; glass spheres, both hollow and solid, and surface-treated glass spheres typically having coupling agents, such as silane coupling agents and/or containing a conductive coating; kaolin, including hard, soft, calcined kaolin, and kaolin comprising various coatings known to the art to facilitate the dispersion in and compatibility with the thermosetting resin; mica, including metallized mica and mica surface treated with aminosilanes or acryloylsilanes coatings to impart good physicals to compounded blends; fedspar and nepheline syenite; silicate spheres; flue dust; cenospheres; fillite; aluminosilicate (atmospheres), including silanized and metallized aluminosilicate; natural silica sand; quartz; quartzite; perlite; tripoli; diatomaceous earth; and synthetic silica, including those with various silane coatings, and the like.

The fibrous filler may include glass fibers, including textile glass fibers such as E, A, C, ECR, R, S, D, and NE glasses and quartz. The fibrous filler may include short inorganic fibers, such as chopped fiber, including processed mineral fibers (e.g., derived from blends having at least one of aluminum silicates), aluminum oxides, magnesium oxides, and calcium sulfate hemihydrate. The fibrous filler may also include single crystal fibers or "whiskers" including silicon carbide, alumina, boron carbide. Certain fibrous fillers may include glass fibers having a diameter of about 5 to about 25 micrometers and a length (e.g., before compounding) of about 0.5 to about 4 centimeters.

When present, the granular filler may be used in an amount of about 0 to about 80 weight percent of the composition (e.g., the composite material for making the resistor grid insulation board). Within this range, it may be desirable to include a granular filler in an amount of at least about 10 weight percent, about 20 weight percent, about 30 weight percent, or about 40 weight percent. Also within this range, it may be desired to include a granular filler in an amount of up to about 70 weight percent, or about 60 weight percent.

When present, the fibrous filler may be used in an amount of about 2 to about 80 weight percent of the composition (e.g., the composite material for making the resistor grid insulation board). Within this range, it may be desirable to include a fibrous filler in an amount of at least about 5 weight percent, about 10 weight percent, or about 15 weight percent. Also within this range, it may be desirable to include a fibrous filler in an amount of up to about 60 weight percent, about 50 weight percent, about 40 weight percent, or about 30 weight percent.

In some embodiments, the one or more fillers may be added to the thermosetting resin without any treatment. In other embodiments, the compound including the thermosetting resin and the filler may be further treated (e.g., on a surface, or a substrate) with one more adhesion promoters (block 46). The one or more adhesion promoters may be added to improve adhesion of the thermosetting resin to the filler and/or to an external coating or substrate.

The adhesion promoters may include chromium complexes, silanes, titanates, zirco-aluminates, propylene maleic anhydride copolymers, reactive cellulose esters and the like. More specifically, the chromium complexes may include VOLAN®™. commercially available from DuPont. The silanes may include molecules having the general structure $(RO)_{(4-n)}SiY_n$, wherein n=1, 2, 3, R is an alkyl or aryl group, and Y is a reactive functional group which can enable formation of a bond with a polymer molecule. More specifically, the silanes may include molecules having the structure $(RO)_3SiY$, such as vinyl-triethoxysilane, vinyl tris (2-methoxy)silane, γ-methacryloxypropyltrimethoxy silane, γ-aminopropyltriethoxysilane, γ-glycidoxypropyltrimethoxysilane, and γ-mercaptopropyltrimethoxysilane. The titanates may include those developed by S. J. Monte et al. in Ann. Chem. Tech Conf. SPI (1980), Ann. Tech Conf. Reinforced Plastics and Composite inst. SPI 1979, Section 16E, New Orleans; and S. J. Monte, Mod. Plastics Int. 14(1984) 6, page 2. The zirco-aluminates may include those described by L. B. Cohen in Plastics Engineering 39 (1983) 11, page 29. The adhesion promoter may be included in the thermosetting resin itself, or coated onto any of the fillers to improve adhesion between the filler and the thermosetting resin. For example, the adhesion promoter may be used to coat a silicate fibrous filler to improve adhesion with the resin.

Once the compound (e.g., including the thermosetting resin, the filler, and/or the adhesion promoter) is prepared, the compound may be molded (e.g., in a mold) into any suitable shape (block 48). For example, the compound may be molded into a resistor grid insulation board as described above with respect to FIG. 2.

The molding compound may be placed into a mold and cured, for example, by heating to a temperature above the glass transition temperature of the thermosetting resin used in the compound (e.g., above 200° C.) (block 50). For example, a molding compound including the thermosetting vinyl ester resins (e.g., as described in U.S. Pat. Nos. 8,409,692 and 8,202,606) may be heated to temperatures between about 100 and 200° C., such as between about 120 and 170° C. A molding compound including the thermosetting phenolic resins (e.g., as described in U.S. Pat. Nos. 8,409,692 and 8,202,606) may be heated to temperatures between about 200 and 350° C., such as between about 250 and 330° C., or between 260 and 320° C. A molding compound including the thermosetting bismaleimide resins (e.g., as described above) may be heated to temperatures between about 200 and 350° C., such as between about 250 and 330° C., or between 260 and 320° C. A molding compound including the thermosetting polyimide and phtalonitrile resins (e.g., as described above) may be heated to the same or similar temperatures as the molding compound including the thermosetting bismaleimide resins. In some embodiments, the cured molding compound may be further post-cured (e.g., in an oven).

The cured molding compound may be evaluated for properties applicable to the resistor grid insulation board during its operation, including thermal oxidative stability, tribological performance, and dimensional stability. Table 1 illustrates such properties for five cured molding compounds, including two molding compounds (e.g., Sample 4 and Sample 5) that include the thermosetting bismaleimide resins as described herein, one molding compound (e.g., Sample 1) that includes the thermosetting vinyl ester resin, and two molding compounds (e.g., Sample 2 and Sample 3) that includes the phenolic resins for comparison.

TABLE 1

Comparative properties of cured molding compounds

| Sample | Polymer | TGA Decomposition Onset in Air (° C.) | RT Tribology Wear Volume (mm³) | RT Tribology Coefficient of Friction | 250° C. (168 h in Air) Exposure 250° C. Weight Loss (%) | 250° C. (168 h in Air) Exposure 250° C. Wear Volume (mm3) | 250° C. (168 h in Air) Exposure 250° C. Coefficient of Friction | 300° C. (100 h in Air) Exposure 250° C. Weight Loss (%) | 300° C. (100 h in Air) Exposure 250° C. Wear Volume (mm3) | 300° C. (100 h in Air) Exposure 250° C. Coefficient of Friction |
|---|---|---|---|---|---|---|---|---|---|---|
| Sample 1 | Vinyl Ester | 356 | 3.09 | 0.44 | 4.81 | 8.42 | 0.64 | 30.32 | Fail | Fail |

TABLE 1-continued

Comparative properties of cured molding compounds

| | | TGA | RT Tribology | | 250° C. (168 h in Air) Exposure | | | 300° C. (100 h in Air) Exposure | | |
| | | | | | 250° C. | | | 250° C. | | |
|---|---|---|---|---|---|---|---|---|---|---|
| Sample | Polymer | Decomposition Onset in Air (° C.) | Wear Volume (mm³) | Coefficient of Friction | Weight Loss (%) | Wear Volume (mm3) | Coefficient of Friction | Weight Loss (%) | Wear Volume (mm3) | Coefficient of Friction |
| Sample 2 | Phenolic | 473 | 0.65 | 0.59 | 2.86 | 113.00 | 0.58 | 26.50 | Fail | Fail |
| Sample 3 | Phenolic | 478 | 0.95 | 0.41 | 2.41 | 117.00 | 0.90 | 21.19 | Fail | Fail |
| Sample 4 | Bismaleimide | 436 | 1.40 | 0.43 | 5.46 | 9.43 | 0.62 | 10.32 | 22.9 | 0.39 |
| Sample 5 | Bismaleimide | 440 | 0.48 | 0.43 | 3.31 | 15.59 | 0.61 | 4.07 | 42.6 | 0.63 |

As noted above, certain vinyl ester resins and certain phenolic resins have been proposed as materials for construction for resistor grid insulation boards because of their electrical properties. Moreover, the vinyl esters resins and the phenolic resins have high glass transition temperatures (e.g., about 140° C., 230° C., respectively) and, therefore, thermally stable. Although the thermosetting bismaleimide resin (and the thermosetting polyimide and phthalonitrile resins) has a similar glass transition temperature to the phenolic resin, it has been found, unexpectedly, that the thermosetting bismaleimide resin (and the thermosetting polyimide and phthalonitrile resins) has far superior tribological performance and dimensional stability. As shown in Table 1, the molding compounds (e.g., Sample 1, Sample 2, and Sample 3) that include the thermosetting vinyl ester resins and phenolic resins show excessive weight loss at elevated temperatures (e.g., about 250° C.) and suffer from insufficient abrasion resistance after thermal exposure (e.g., about 168 hours at about 250° C., about 100 hours at about 300° C.), which are important factors relating to the stability of these materials in resistor gird applications. The bismaleimide compounds (e.g., Sample 4 and Sample 5) have much lower coefficients of friction and weight loss.

Figure 4:
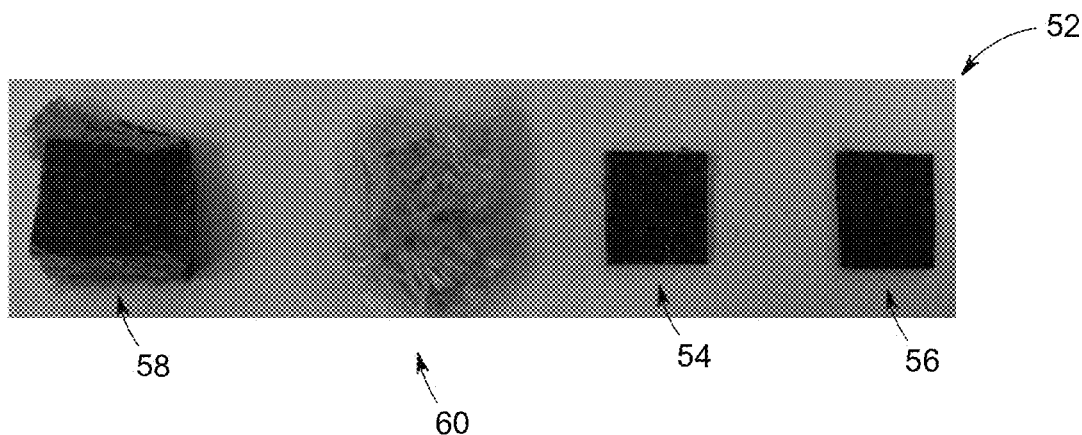
FIG. 4 is a pictorial comparison of four cured molding compounds forming composite materials for insulation boards, in accordance with as aspect of the present disclosure.

To help illustrate, FIG. 4 includes comparative images of the four cured molding compounds, including two cured molding compounds 54, 56 (e.g., Sample 4 and Sample 5) that include the thermosetting bismaleimide resins, and two cured molding compounds 58, 60 (e.g., Sample 1 and Sample 2) that include the thermosetting vinyl ester resins and phenolic resins, respectively, after thermal exposure of about 440 hours at about 250° C. As illustrated, the cured molding compounds 54, 56 (e.g., Sample 4 and Sample 5) that include the thermosetting bismaleimide resins show no substantial dimensional changes after the prolonged thermal exposure. On the other hand, the cured molding compound 58 (e.g., Sample 1) that includes the vinyl ester resin exhibits insufficient dimensional stability upon prolonged exposure to elevated temperature (e.g., about 440 hours, about 250° C.). While the cured molding compound 60 (e.g., Sample 2) that includes the phenolic resin shows enhanced thermal performance, as indicated by the high thermal oxidative degradation onset (e.g., about 473° C.) noted in Table 1, FIG. 4 shows that the cured molding compound 60 (e.g., Sample 2) that includes the phenolic resin exhibits insufficient dimensional stability upon prolonged exposure to elevated temperature. In other words, as indicated by Table 1, the cured molding compounds 54, 56 (e.g., Sample 4 and Sample 5) that include the thermosetting bismaleimide resins are unexpectedly superior to the cured molding compounds 58, 60 (e.g., Sample 1 and Sample 2) that include the thermosetting vinyl ester resins and phenolic resins with regard to the abrasion resistance after exposure to elevated temperatures. In addition, as indicated by FIG. 4, the cured molding compounds 54, 56 (e.g., Sample 4 and Sample 5) that include the thermosetting bismaleimide resins are unexpectedly superior to the cured molding compounds 58, 60 (e.g., Sample 1 and Sample 2) that include the thermosetting vinyl ester resins and phenolic resins with regard to dimensional stability upon prolonged exposure to elevated temperatures. Accordingly, it is believed that the use of the thermosetting bismaleimide resins disclosed herein provide unexpectedly superior properties that are of particular concern for resistor grid insulation board constructions.

This written description uses examples to disclose the embodiments, including the best mode, and also to enable any person skilled in the art to practice the present disclosure, including making and using any devices or systems and performing any incorporated methods. The patentable scope of the present disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:
1. An insulation board for a resistor grid, the insulation board comprising:
   a substantially planar element made of a composite material, wherein the composite material comprises a nitrogen-containing aromatic thermosetting polymeric resin comprising a thermosetting bismaleimide resin and a filler disposed within the nitrogen-containing aromatic thermosetting polymeric resin, and wherein the thermosetting bismaleimide resin is formed from an amorphous resin formed from one or more bismaleimide monomers such that the thermosetting bismaleimide resin is at least 95 percent amorphous; and
   one or more rows of transverse pin holes disposed along a length of the substantially planar element and configured to engage pins of one or more resistive elements of the resistor grid, wherein the insulation board does not include a metal supporting structure.
2. The insulation board of claim 1, wherein the thermosetting bismaleimide resin is formed from a eutectic mixture of two or more bismaleimide monomers.

3. The insulation board of claim 1, wherein the filler comprises a granular filler, a fibrous filler, or a combination thereof.

4. The insulation board of claim 1, wherein the filler comprises a granular filler present in the composite material in an amount of approximately 1 to 80 weight percent based on a weight of the composite material.

5. The insulation board of claim 1, wherein the filler comprises a fibrous filler present in the composite material in an amount of approximately 2 to 80 weight percent based on a weight of the composite material.

6. The insulation board of claim 1, wherein the composite material comprises an adhesion promoter.

\* \* \* \* \*